US012746113B2

(12) United States Patent
Maroscheck et al.

(10) Patent No.: US 12,746,113 B2
(45) Date of Patent: Sep. 29, 2026

(54) INJECTOR FOR AN INTRAOCULAR LENS

(71) Applicant: IOLUTION GmbH, Hamburg (DE)

(72) Inventors: Christoph Maroscheck, Hamburg (DE); Thomas Zehnder, Zug (AT); Maximiliano Gutierrez, Hamburg (DE)

(73) Assignee: IOLUTION GmbH, Hamburg (DE)

( * ) Notice: Subject to any disclaimer, the term of this patent is extended or adjusted under 35 U.S.C. 154(b) by 419 days.

(21) Appl. No.: 18/560,995

(22) PCT Filed: May 16, 2022

(86) PCT No.: PCT/EP2022/063167
§ 371 (c)(1),
(2) Date: Nov. 15, 2023

(87) PCT Pub. No.: WO2022/243233
PCT Pub. Date: Nov. 24, 2022

(65) Prior Publication Data

US 2024/0268951 A1 Aug. 15, 2024

(30) Foreign Application Priority Data

May 17, 2021 (DE) ........................ 10 2021 112 682

(51) Int. Cl.
*A61F 2/16* (2006.01)

(52) U.S. Cl.
CPC ............ *A61F 2/167* (2013.01); *A61F 2/1667* (2013.01)

(58) Field of Classification Search
CPC ...... A61F 2/167; A61F 2/1667; A61F 2/1672; A61F 2/1678
See application file for complete search history.

(56) References Cited

U.S. PATENT DOCUMENTS

| | | | | |
|---|---|---|---|---|
| 11,026,780 | B2 * | 6/2021 | Maroschek | A61F 2/167 |
| 11,931,246 | B2 * | 3/2024 | Bayer | A61F 2/1672 |
| 2009/0112223 | A1 | 4/2009 | Downer et al. | |
| 2013/0006259 | A1 | 1/2013 | Sanger | |
| 2019/0151078 | A1 | 5/2019 | Watanabe et al. | |

FOREIGN PATENT DOCUMENTS

| | | | |
|---|---|---|---|
| EP | 2150204 | B1 | 9/2010 |
| EP | 3476375 | B1 | 5/2019 |
| EP | 3738556 | A1 | 11/2020 |
| JP | H0779826 | A | 8/1995 |
| WO | 2011126144 | A1 | 10/2011 |

* cited by examiner

*Primary Examiner* — Bruce E Snow
(74) *Attorney, Agent, or Firm* — Smartpat PLC

(57) ABSTRACT

An injector for an intraocular lens includes a housing with a cannula, a receiving chamber for the intraocular lens, and a plunger that can be moved within the housing. The plunger is adapted to move the intraocular lens out of the receiving chamber and through the cannula. The injector includes a rotary element for moving the plunger. The rotary element is mounted on the plunger for rotation and axial translation thereon.

13 Claims, 7 Drawing Sheets

INJECTOR FOR AN INTRAOCULAR LENS

CROSS-REFERENCE TO RELATED APPLICATION

This application is a national stage application, filed under 35 U.S.C. § 371, of International Patent Application PCT/EP2022/063167, filed on May 16, 2022, which claims the benefit of German Patent Application DE 10 2021 112 682, filed on May 17, 2021.

TECHNICAL FIELD

The disclosure relates to an injector for an intraocular lens. More particularly, the disclosure relates to an injector designed as a disposable or single-use system, which can be used to dispense an intraocular lens and position it in a patient's eye. The disclosure furthermore relates to a method for dispensing an intraocular lens from an injector.

BACKGROUND

Injectors have become established for inserting intraocular lenses as a replacement for the natural lens of the eye, as is particularly the case in the treatment of cataracts.

Such an injector comprises a plunger which serves to transfer the lens through a cannula and into the patient's eye.

An advantage of such injectors in particular is that they allow to transfer the lens into the eye even in a folded state, so that the passage or incision required for the cannula is smaller in cross section than an incision that would have to be cut for introducing a non-folded lens into the eye.

Once the lens has reached the tip of the cannula, the advancement distance still required will be quite small. In particular, it will usually be less than 12 mm, even for lenses with a haptic.

Moreover, due to the tapering cannula, the force required for advancement can initially increase to then suddenly drop when the lens has partially left the cannula. As such it may be difficult to maintain the exact position while pressing the plunger.

Patent document EP 2 150 204 B1 therefore contemplates for the plunger to have a thread which allows to convert a rotary movement on the handpiece of the plunger into a linear movement, i.e., translation, thereof.

Since the user would have to turn extensively for the entire dispensing process, the above-mentioned patent document suggests using a motion link guide or cam track with locking balls so that the thread of the plunger is only engaged when this is desired by the user.

A drawback of the injector according to the teachings of this document is that the user first has to actuate the ring with the locking detent in order to bring the balls into engagement with the thread. Then, the user has to reach around so as to hold the injector on the housing and to then further advance the plunger by turning the handpiece of the plunger rod.

The reaching around, i.e., changing of the grip, may result in mispositioning. Furthermore, it is hardly possible in this way to repeatedly switch between using the rotary element and advancing by pressing the handpiece. However, switching back to manual advancement might make sense depending on the situation, especially when the lens has already partially come out and is optimally positioned. Also, there are users who preferentially tend to advance the lens either by using a rotary element or by pressing.

Furthermore, the injector according to the prior art described above has a quite complex configuration. In particular, metal balls are usually used for a locking detent, so that the injector is partly made of plastics material and partly of metal, which in turn makes it difficult to dispose of or recycle.

SUMMARY

The disclosure is based on the object of at least mitigating the drawbacks of the prior art mentioned above.

More particularly it is an object of the disclosure to provide an injector for dispensing an intraocular lens, which is both easily manufactured and provides for simple and safe use.

The object is achieved by an injector for an intraocular lens and by a method for dispensing an intraocular lens from an injector as claimed.

Preferred embodiments and refinements will be apparent from the subject-matter of the dependent claims, the description and the drawings.

The application relates to an injector for an intraocular lens, which comprises a housing with a cannula, a receiving chamber for the intraocular lens, and a plunger that can be moved within the housing.

The receiving chamber may in particular also be formed integrally with the cannula as a single component which is coupled to a main housing of the injector, for example.

According to one embodiment, a cartridge containing the intraocular lens can be placed on the receiving chamber. The lens can then be transferred into the receiving chamber using a folding member, whereby it will be folded at the same time.

By advancing the plunger, the lens can then be transferred to the tip of the cannula and dispensed into the patient's eye.

The injector comprises a rotary element for moving the plunger, and the rotary element is mounted on the plunger both for rotation and for axial translation without being rotated.

In terms of being mounted for rotation, the rotary element may in particular be guided on a plunger rod of the plunger. In particular, the rotary element and the plunger rod may define an interference fit. The rotary element can thus be turned against the friction of the interference fit and sits on the plunger rod without play.

The plunger, in turn, is axially displaceable in the distal direction relative to the rotary element.

Thus, in addition to an advancement by using the rotary element, it is also possible for the plunger to be advanced by hand by pressing a handpiece at the proximal end of the plunger.

In particular, in a starting position, the rotary element can be spaced apart from a main housing of the injector such that a thread of the rotary element does not engage with a corresponding threaded structure of the main housing of the injector.

Therefore, the user can initially push the plunger forward by pressing on a proximal end of the plunger.

Then, the rotary element will engage on a seat.

Now, further advancement can be facilitated using the rotary element, by virtue of engagement of a thread of the rotary element, so that the plunger can now also be shifted forward using the rotary element.

According to one embodiment it is contemplated that, once the rotary element has been engaged on the seat, the plunger can still also be further advanced by pressing on the proximal end of the plunger.

The user can therefore switch, as desired, between advancement by pressing on the plunger or advancement by turning the rotary element.

The seat for the rotary element is preferably provided adjacent to a finger flange, in particular a wing-type finger flange or grip.

This grip can serve as a counter-holder for the user when pressing the plunger forward.

To operate the rotary element, the user only needs to place the fingers of one hand on the rotary element, and the user's hand placed at the proximal end can be used for guidance during the rotation.

If the user now decides to not completely press the lens out of the cannula by turning the rotary element, the housing with the rotary element whose thread is now engaged, may just serve as a counter-holder for completing the remaining push-out process by pressing on the plunger.

The disclosure provides for a simple design of an injector consisting of just a few parts. In particular metal parts can be at least largely, preferably completely, dispensed with.

Furthermore, as already mentioned above, particularly simple operation is facilitated, and preferably also easy switching between advancement by turning and advancement by pressing.

The injector is preferably adapted so that the thread of the rotary element engages with the seat when the intraocular lens is already located in the cannula.

Thus, the transfer from the receiving chamber into the cannula which preferably tapers conically in the forward direction, is preferably performed solely by pressing on the distal end of the plunger.

It is in particular contemplated that the thread engages with the seat when the intraocular lens is located immediately in front, i.e. upstream, of the tip of the cannula. Thus, it is contemplated that only the last part of the dispensing process, namely the pushing of the lens out of the cannula's tip, can be carried out using the rotary element.

In one embodiment, the rotary element is secured on the plunger against displacement in the distal direction by a locking ring.

The locking ring may in particular be slotted so that it can be deflected apart to be fitted around the plunger rod.

This allows for easy manufacturing and assembly.

The locking ring is also effective as a stop which entrains the plunger forward when the rotary element is turned.

It will be appreciated that when the rotary element is used to advance the plunger and then further advancement is achieved by pressing on the plunger, the rotary element will only come to rest against the locking ring again when it is rotated further forward accordingly. However, such a situation will rarely occur when using the injector. If the user decides to switch back from advancement by turning to an advancement by pressing on the plunger, the lens will usually already have been positioned as desired and will then only be pressed out by a final single press on the plunger to then unfold in the eye.

In one embodiment, a resilient stopper is provided between the plunger and the housing, which is effective as a stop for the plunger in its end position.

The resilient stopper may, for example, be inserted into the housing or fitted onto the plunger.

In this way, a "soft" stop is provided in the end position, which makes reaching the end position well perceivable haptically.

In one embodiment, the plunger is latched in a main housing of the injector in a starting position.

The plunger may in particular comprise a latching hook, which latches into a recess in the main housing during assembly. The plunger can now no longer be retracted.

If, on the other hand, the plunger is now advanced in the distal direction, the latching hook will spring in and allow the plunger to be advanced further.

The plunger rod may have a cross-shaped cross section.

This makes it easier to mount the plunger rod in the housing.

Furthermore, the plunger rod may become thicker in the proximal direction step by step.

More particularly, a front part of the plunger rod may have a smaller outer diameter than a rear part of the plunger rod.

The rear part of the plunger rod is therefore more robust and can be guided in a main housing, whereas the front part protrudes from the main housing and into the receiving chamber or, when further advanced, into the cannula.

The seat on the housing may have a segmented external thread for the rotary element.

This makes it easier to engage the internal thread of the rotary element.

A thread in the sense of the disclosure is understood to mean any engaged components which allow to convert a rotary movement of the rotary element into an axial linear movement, i.e. translation, of the plunger.

In particular, the engagement features on the seat on the main housing do not need to be in the form of threads having a pitch, rather it will be sufficient to provide ribs which engage with the internal thread of the rotary element.

In one embodiment, the rotary element engages on the seat after an advancement of the plunger by more than 10 mm and/or by less than 30 mm.

Solely by rotating the rotary element, the plunger is preferably displaceable by more than 5 mm, more preferably by more than 8 mm, and/or by less than 15 mm, more preferably by less than 12 mm.

The rotary element may have an internal thread with a pitch between 1.5 and 7 mm.

Furthermore, the rotary element may have an outer diameter between 18 and 28 mm.

The disclosure furthermore relates to a method for dispensing an intraocular lens from an injector. More particularly, the injector described above can be used to carry out the method.

The method can in particular be performed for test purposes, such as a functional test of the injector.

According to the method, the lens is initially arranged inside a receiving chamber of the injector in a folded state.

The lens may in particular be folded by closing a lid having a folding member.

Thereafter, the lens is transferred from the receiving chamber into a cannula by pressing the handpiece of an axially displaceable plunger. The cannula in particular tapers towards a distal end thereof.

A rotary element mounted on a plunger rod engages on a seat for the rotary element when the intraocular lens is located inside the cannula.

The plunger can then be advanced either by further pressing on the handpiece and/or by turning the rotary element in order to dispense the intraocular lens from the cannula.

Initially, transferring the lens from the receiving chamber into the cannula is done exclusively by pressing on the plunger.

This has the advantage that this step is achieved relatively quickly.

In particular, this method step can be performed when the cannula has not yet been introduced into the patient's eye.

This method step may in particular be carried out by the eye surgeon's assistant.

If the rotary element and the plunger rod form an interference fit, a haptically perceivable resistance will indicate that the rotary element has now engaged on the seat.

The assistant can now hand over the prepared injector to the eye surgeon who is then fully free as to whether he or she prefers to press the lens into the eye by pressing on the plunger or by using the rotary element.

BRIEF DESCRIPTION OF THE DRAWINGS

The subject-matter of the invention will now be explained in more detail with reference to an exemplary embodiment by way of the drawings of FIGS. 1 through 9.

DETAILED DESCRIPTION

Figure 1:
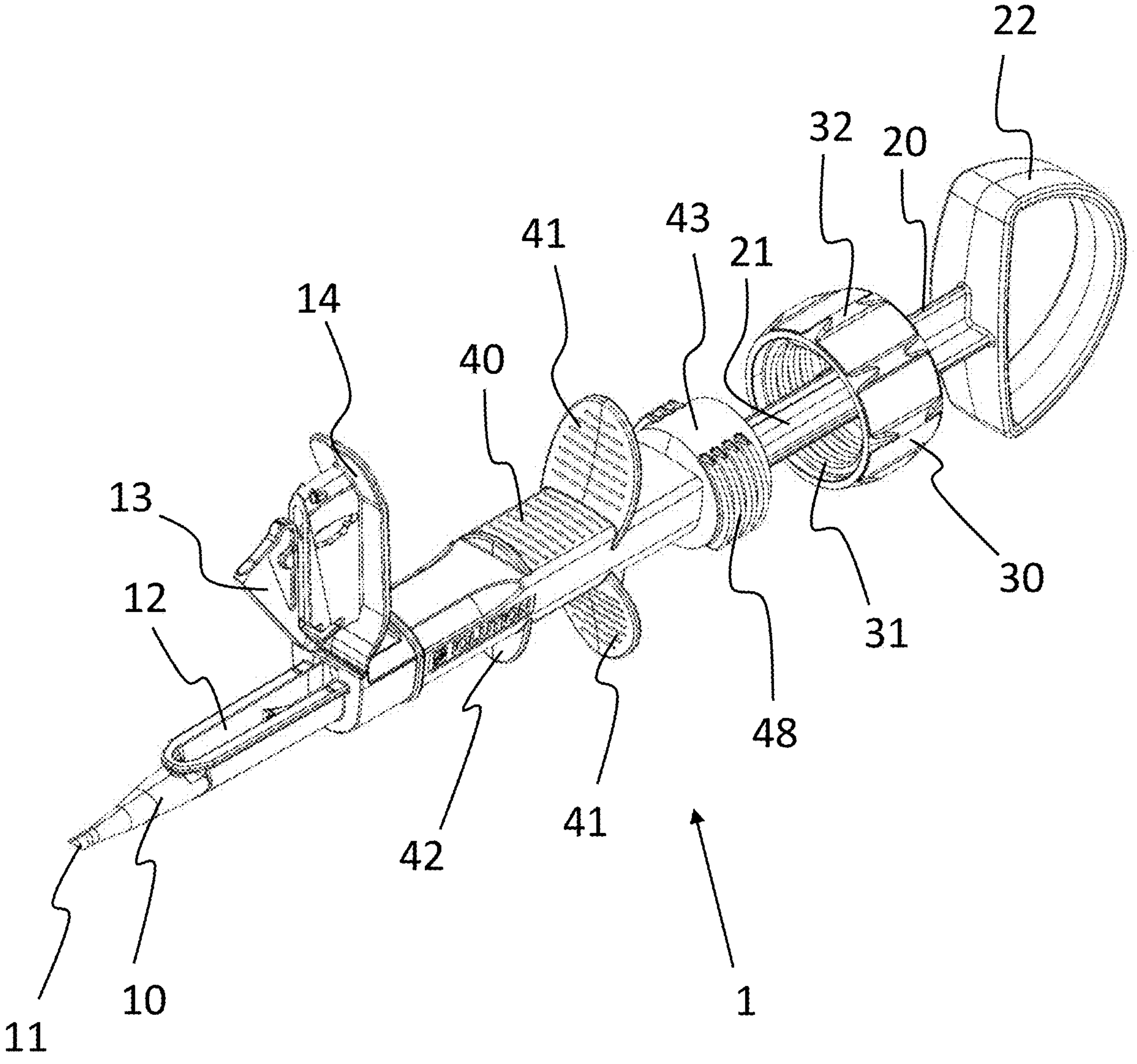
FIGS. 1 to 4 are isometric views of an exemplary embodiment of an injector in operating states thereof. Thus, it is illustrated how the injector is employed to dispense an intraocular lens.

FIG. 1 is an isometric view of an exemplary embodiment of an injector 1.

Injector 1 comprises a cannula 10 having a tip 11 through which an intraocular lens (not shown) can be dispensed into the eye of a patient (not shown).

For this purpose, the intraocular lens is inserted into the receiving chamber 12 and is then pressed out of the cannula 10 using the plunger 20.

In this exemplary embodiment, an intraocular lens that is located in a cartridge (not shown) can be introduced into the receiving chamber 12 by first placing the cartridge on the injector, in particular on the front part thereof comprising the cannula 10 and the receiving chamber.

What is shown here is the not yet fully assembled state, in which the movable folding member 13 has not yet been inserted into the carrier 16.

In the assembled state, a pin 18 of the folding member 13 will sit in the motion link guide, or cam track, of the carrier. This allows for a predefined mobility of the folding member 13 while the lens is being pressed out.

Before the lens is pressed out, the lid 14 fully assembled with the folding member is closed and the folding member 13 coupled to the lid 14 transfers the intraocular lens into the receiving chamber 12 where the lens is immediately folded. The folding member 13 is usually pushed forward in the lid 14 prior to the folding, and then the lid 14 can be closed.

The following drawings neither show how the lid with the folding member is closed.

The basic principle of the invention can however be transferred to all types of injectors for intraocular lenses, especially to those that are already preloaded with a lens.

The injector 1 further comprises the main housing 40 inside which the plunger 20 is guided.

Plunger 20 comprises the plunger rod 21 projecting into the main housing 40 and which comprises the handpiece 22 at its proximal end.

FIG. 1 shows the starting position of the injector 1, that is the operating state before the injector 1 is used.

In this operating state, the rotary element 30 is mounted on the plunger rod 21 for rotation and is still spaced apart from the seat 43 for the rotary element 30.

The rotary element 30 has an internal thread 31.

In this exemplary embodiment, the rotary element 30 has a substantially circular cylindrical shape and has a profiled contour 32 in order to allow for a better grip.

The user can now advance the plunger 20 until the rotary element 30 engages on the seat 43.

Seat 43 has a thread 48 which, in this exemplary embodiment, has a segmented configuration in order to facilitate demolding of the thread 31 of the rotary element 30 from an injection molding tool.

Adjacent to the seat in the distal direction, a wing-type finger flange 41 is provided, where the user can hold the injector 1, for example with the index finger and ring finger, and which thus provides a counter-holder when the user advances the plunger 20 using the handpiece 22.

In this way, the injector can in particular also be used with a single hand by pushing the handpiece 22 forward with the palm of the hand while two fingers hold the injector 1 on the wing-type finger flange 41.

Behind the wing-type grip 41 in the distal direction, there is another grip 42 provided on the underside, which can optionally be used, for example for fine adjustment of the position of the tip 11 of the cannula 10 or to serve as a counter-holder for the middle finger.

Figure 2:
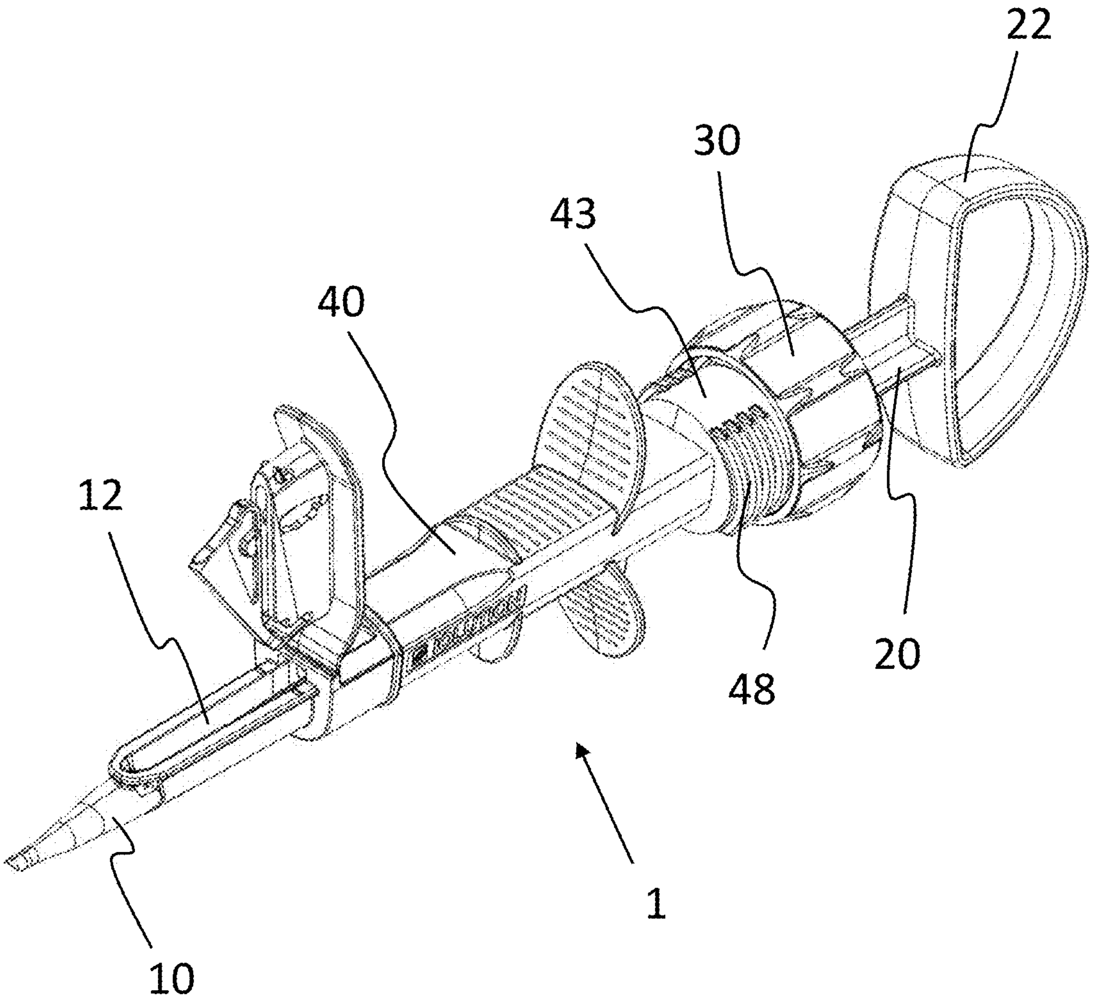

As shown in FIG. 2, the plunger 20 is initially advanced until the rotary element 30 engages on the seat 43 which, in this exemplary embodiment, defines the proximal end of the main housing 40.

The intraocular lens will now already have been transferred from the receiving chamber 12 into the cannula 10. It will be appreciated that the lid 14 will be closed in this situation (not shown).

In fact, the rotary element 30 can now be moved further in the distal direction relative to the plunger 20. However, due to an interference fit between the rotary element 30 and the plunger 20, the user will feel a resistance which signals that the intraocular lens is now ready to be pushed into the eye.

Figure 3:
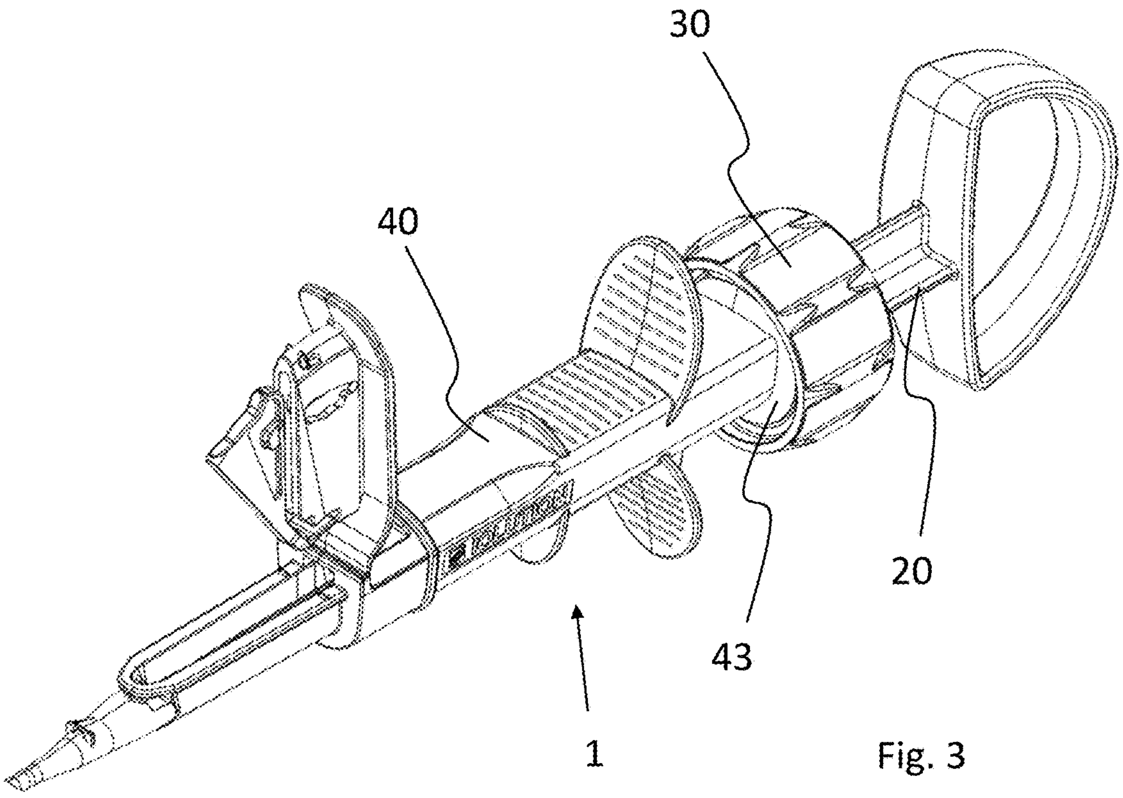
Figure 4:
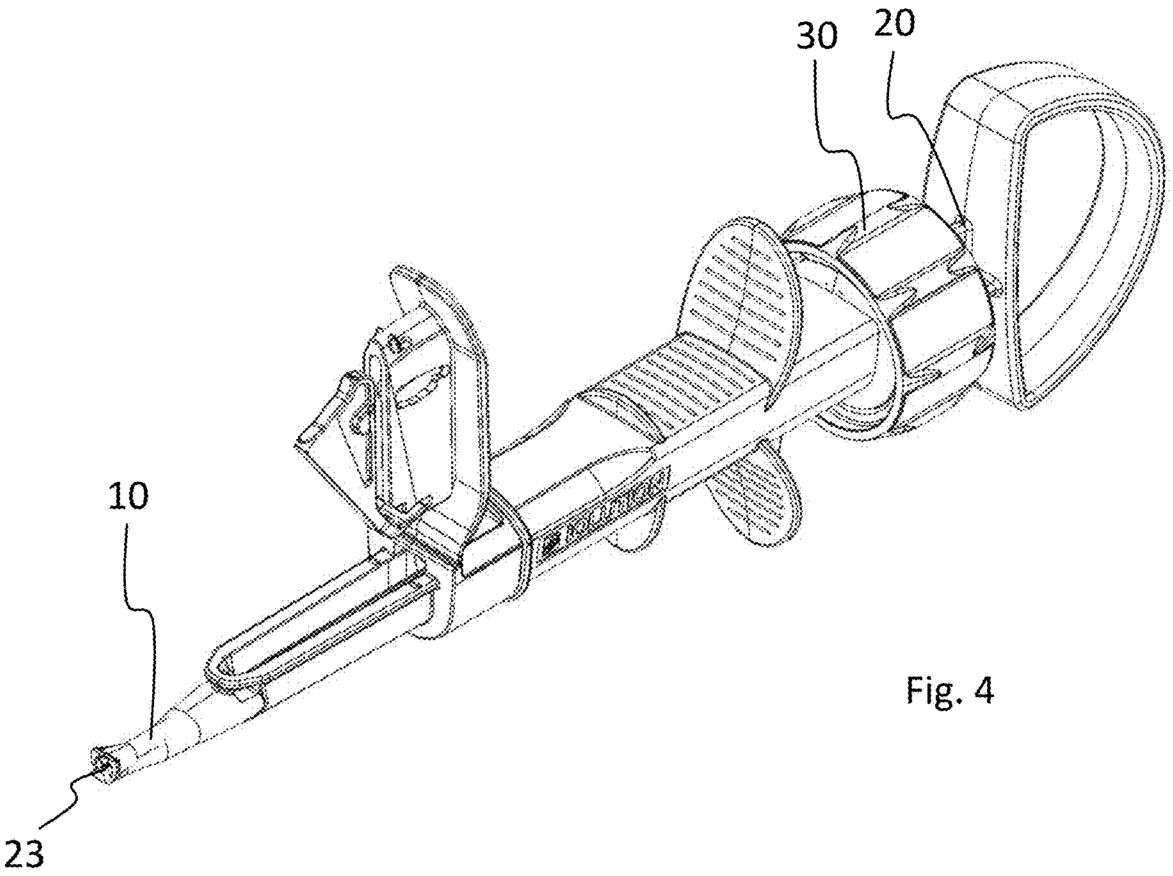

Now, as illustrated further by way of FIGS. 3 and 4, the user can turn the rotary element 30 in order to further advance the plunger 20.

Alternatively, the user can also continue to push the handpiece 22 forward so as to push the intraocular lens out of the cannula 10 without using the rotary element 30.

If the user uses the rotary element, he or she will be able to turn the rotary element 30 until the plunger 20 abuts in its end position, as shown in FIG. 4.

Figure 6:
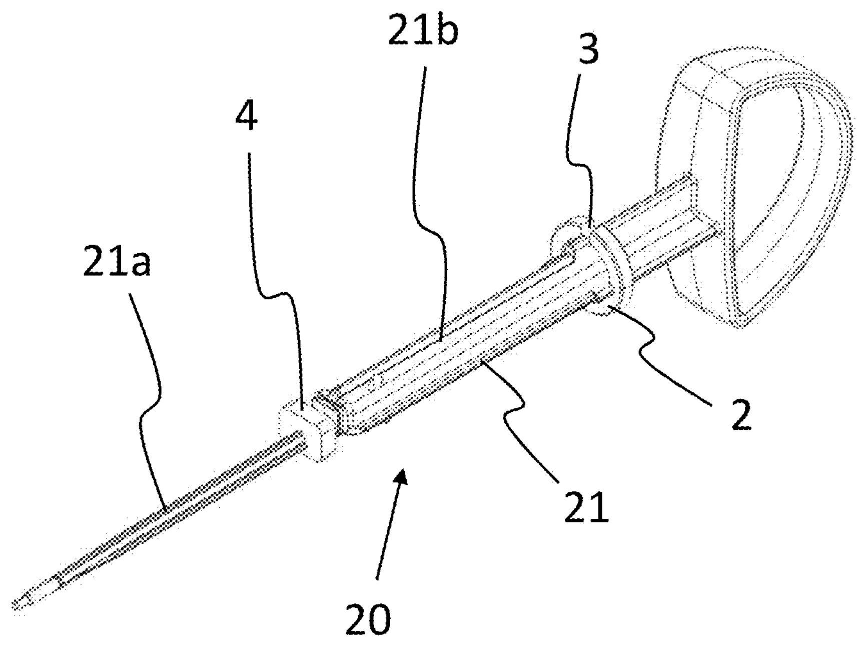
FIG. 6 is an isometric view of the plunger.

Preferably, the handpiece 22 does not come into contact with the seat 43 in the end position, rather the end position is defined solely by a resilient stopper (cf. 4 in FIG. 6).

The intraocular lens has now been transferred into the patient's eye.

Figure 5:
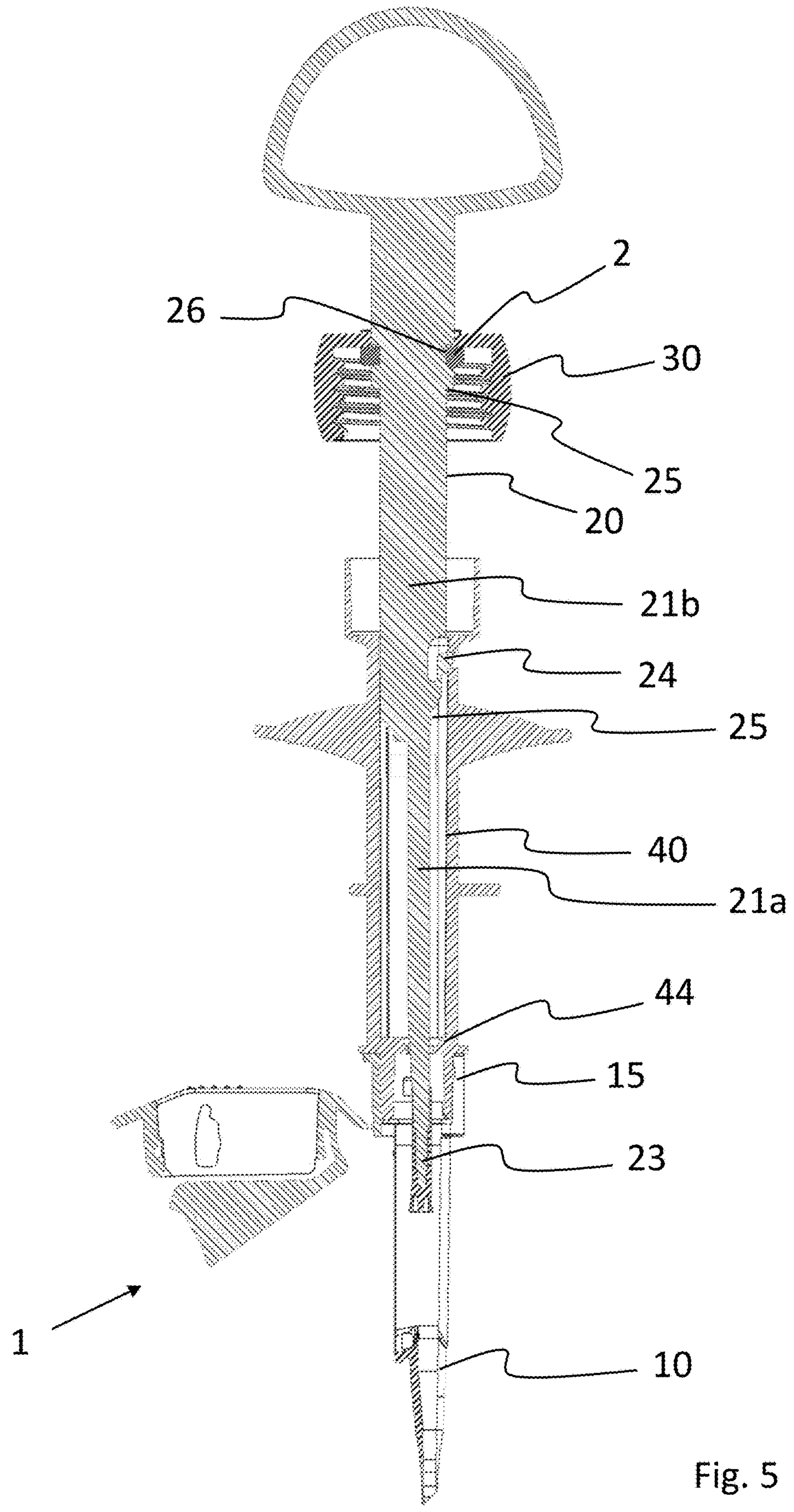
FIG. 5 is a longitudinal sectional view of the injector.

FIG. 5 is a longitudinal sectional view of the injector in its initial state or starting position.

In this exemplary embodiment, the front housing part comprising the cannula 10 has a groove 15 by which it is secured to the main housing 40. That is, the cannula 10 can be snap-fitted to the main housing 40.

The plunger rod 21 is divided into several sections.

A front section 21*a* has a smaller diameter than section 21*b* therebehind.

Section 21*a* serves to accommodate the tip 23 made of resilient material.

A guide 44 for the front section 21*a* of the plunger rod 21 is provided in the distal front portion of the main housing 40.

A section 21*b* of the plunger rod therebehind is guided in the main housing 40. In this section, the plunger rod 21 has a latching hook 24 which is locked in the main housing 40 during assembly and then only allows the plunger 20 to be moved in the distal direction.

The rear section 21*b* of the plunger rod 21 first has a step 25 within the range of the rotary element 30.

Behind the step follows a groove 26 in which the locking ring 2 sits. The locking ring 2 defines a stop for the rotary element 30 in the distal direction.

In the initial state, the rotary element 30 is located at this stop.

In order to provide a stop in the end position of the plunger 20, a resilient stopper 4 is fitted on the plunger 20 in this embodiment.

The front guide 44 defines a wall against which the resilient stopper 4 comes to rest in the end position and thus resiliently stops and terminates the advancement.

According to another embodiment (not illustrated), the resilient stopper may also be integrated into the main housing instead of being fitted on the plunger.

FIG. 6 shows a perspective view of the plunger 20 together with the locking ring 2. The locking ring 2 has a slot 3 so that it can be expanded and inserted into the groove of the plunger rod 21.

Both the front section 21*a* of the plunger rod and the rear section 21*b* of the plunger rod 21 are cross-shaped in cross section in order to slide in a corresponding guide of the housing of the injector.

Furthermore, the resilient stopper 4 sits on the front section 21*a* of plunger rod 21.

Figure 7:
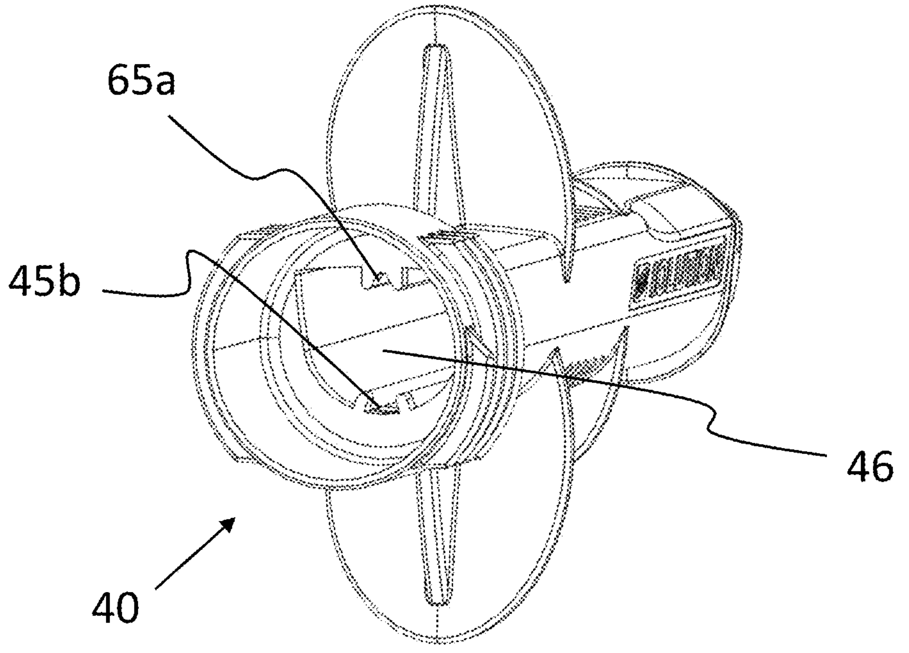
FIG. 7 is a perspective view of the proximal end of the main housing.

It provides for resilient abutment when the plunger 20 reaches its end position. FIG. 7 is a perspective view of the proximal end of the main housing 40.

The main housing has a passage 46 for the plunger rod, more precisely for the rear section (21*b*) of the plunger rod.

An upper guide rail 45*a* and a lower guide rail 45*b* protrude into the passage 46.

These guide rails provide guidance for the plunger rod inside the main housing 40.

Figure 8:
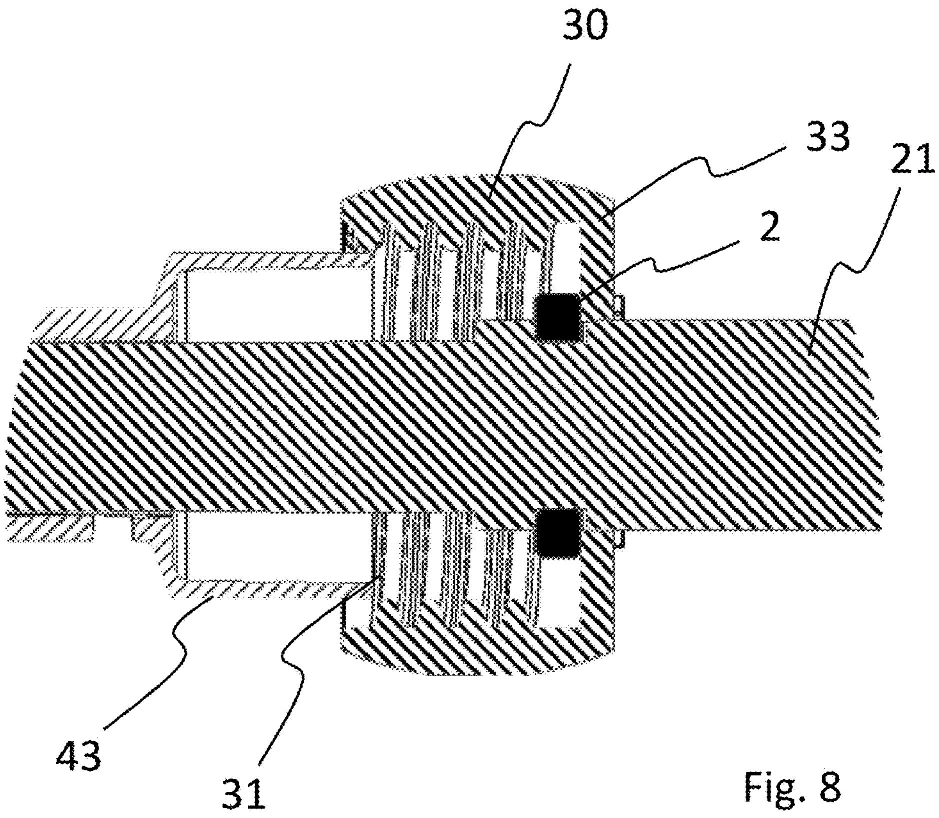
FIGS. 8 and 9 are longitudinal sectional views of details in the vicinity of the rotary element in different operating states of the injector.

FIG. 8 shows a detailed view of the position of the rotary element when it engages on seat 43. This position corresponds to the illustration according to FIG. 2.

The rotary element 30 with its wall 33 mounted for rotation on the plunger rod 21, is moved forward together with the plunger rod 21, i.e. in the distal direction, until the thread 31 engages with the thread of the seat 43.

Figure 10:
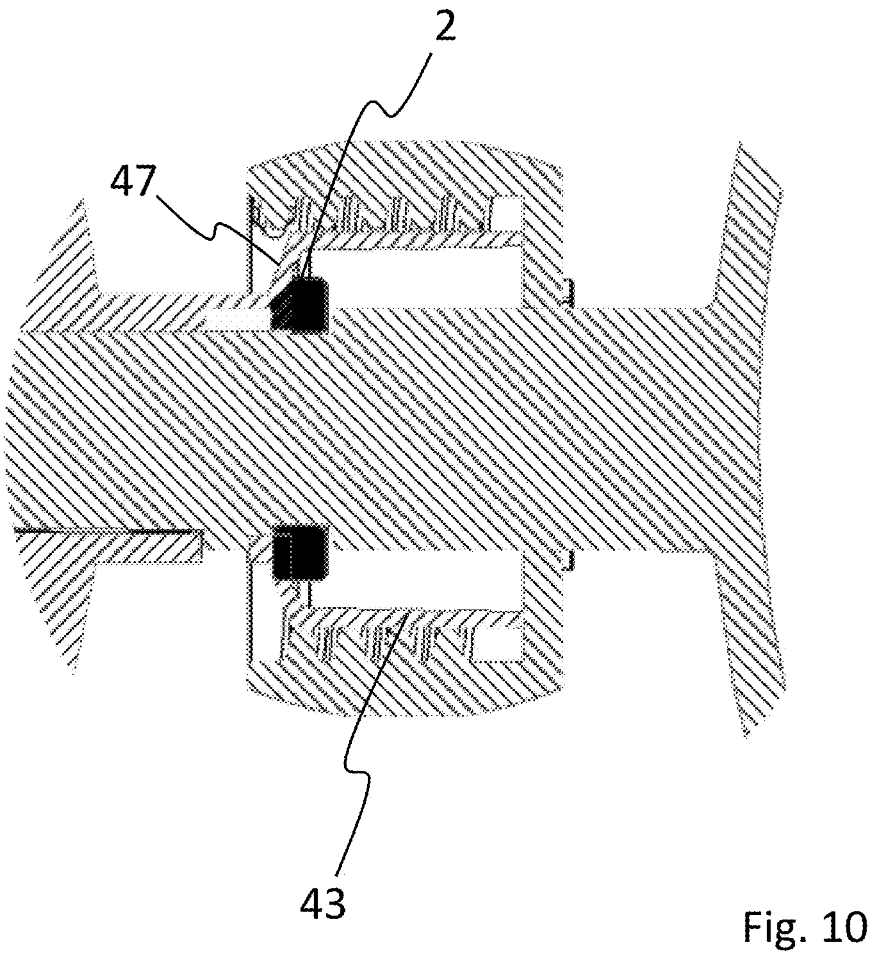
FIG. 10 shows the plunger with the locking ring being in a proximal position.

If the user now continues to press the proximal end of the plunger 20, the plunger rod 21 will move further forward until the locking ring reaches a stepped wall of the seat (FIG. 10).

Figure 9:
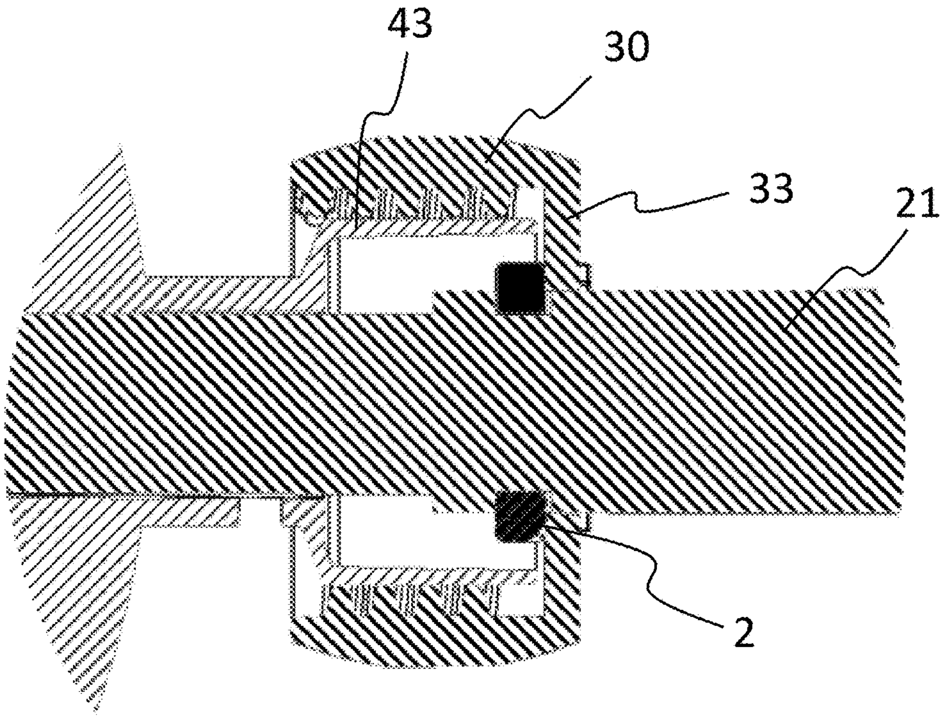

If the user now turns the rotary element 30, as shown in FIG. 9, in order to push out the intraocular lens as slowly as possible, the wall 33 abutting on the locking ring 2 will push the plunger rod 21 forward until the rotary element 30 reaches the end position.

Further rotation of the rotary element 30 will then no longer be possible because further advancement of the plunger will be blocked by the stopper. So, the locking ring 2 will not engage on wall 47.

The disclosure permitted to provide a simple but very easy to use injector for intraocular lenses. It in particular allows to optionally use a rotary element while the intraocular lens is dispensed from the cannula of the injector.

LIST OF REFERENCE NUMERALS

1 Injector
2 Locking ring
3 Slot
4 Resilient stopper
10 Cannula
11 Tip
12 Lens receptacle
13 Folding member
14 Lid
15 Groove
16 Carrier
17 Motion link guide
18 Pin
20 Plunger
21 Plunger rod
22 Handpiece
23 Tip
24 Latching hook
25 Step
26 Groove
30 Rotary element
31 Internal thread
32 Profiled contour
40 Main housing
41 Wing-type finger flange
42 Front grip
43 Seat for the rotary element
44 Guide for 21*a*
45*a* Upper guide rail
45*b* Lower guide rail
46 Passage for 21*b*
47 Wall
48 Thread

The invention claimed is:

1. An injector for an intraocular lens, comprising:

a housing extending between a distal end and a proximal end, the housing comprising
a cannula at the distal end, and
a seat having an external thread at the proximal end;

a receiving chamber for the intraocular lens, the receiving chamber being arranged in or adjacent to the distal end of the housing and communicating with the cannula;

a plunger, the plunger being movable within the housing and adapted to move the intraocular lens from the receiving chamber through the cannula; and a rotary element having an internal thread configured to mesh with the external thread of the seat, wherein the plunger comprises a locking ring disposed within the rotary element, and wherein the plunger is axially movable by turning the rotary element relative to the housing when the internal thread of the rotary element engages the external thread of the seat while the locking ring abuts a proximal wall of the rotary element.

2. The injector of claim 1, wherein, in a starting position, the rotary element is spaced apart from the seat, and wherein the rotary element is displaceable together with the plunger until the rotary element comes into contact with the seat and the internal thread of the rotary element engages the external thread of the seat.

3. The injector of claim 2, wherein the injector is adapted so that the internal thread of the rotary element engages with the external thread of the seat when the intraocular lens is located inside the cannula.

4. The injector of claim 3, wherein the intraocular lens can be pushed out of the cannula by turning the rotary element.

5. The injector of claim 2, wherein the injector is adapted so that the internal thread of the rotary element engages with the external thread of the seat when the intraocular lens is located immediately in front of a tip of the cannula.

6. The injector as claimed in claim 2, wherein the intraocular lens is arranged in the receiving chamber in a folded state; and/or wherein the plunger is latched to the housing; and/or wherein the rotary element is substantially in form of a circular cylinder having a central opening in the proximal wall which, in cooperation with a plunger rod, defines a rotary bearing; and/or wherein the plunger rod has a cross-shaped cross section; and/or wherein the seat for the rotary element has a segmented external thread; and/or wherein the rotary element engages on the seat after an advancement of the plunger by more than 10 mm and/or by less than 30 mm; and/or wherein the plunger is displaceable using the rotary element by more than 5 mm, and/or by less than 15 mm; and/or wherein the internal thread of the rotary element has a pitch between 1.5 and 7 mm; and/or wherein the housing, the plunger, and the rotary element are made of plastic material; and/or wherein the plunger and the rotary element define a rotary bearing with an interference fit; and/or wherein the rotary element has an outer diameter between 18 and 28 mm.

7. The injector as claimed in claim 1, wherein the rotary element on the plunger is secured against displacement in a distal direction by the locking ring.

8. The injector as claimed in claim 1, wherein, once the rotary element has reached its end position, the plunger can be further advanced using a handpiece.

9. The injector as claimed in claim 1, wherein the locking ring is axially displaceable within the rotary element between the proximal wall of the rotary element and a stepped wall of the seat, whereby, once the rotary element has reached its end position, the plunger can be further advanced using a handpiece over a distance of 1 to 8 mm.

10. The injector of claim 1, wherein the plunger comprises a plunger rod having a front section and a rear section, the front section being configured to extend into the cannula and having a smaller diameter than the rear section, wherein the rear section has a cross-shaped cross section, and wherein the housing comprises guide rails configured to receive and axially guide the rear section of the plunger rod.

11. An injector for an intraocular lens, comprising:

a housing with a cannula;

a receiving chamber for the intraocular lens;

a plunger, the plunger being movable within the housing and adapted to move the intraocular lens from the receiving chamber through the cannula; and a rotary element for moving the plunger, the rotary element being mounted on the plunger for rotation and axial translation thereon, wherein, at an end position, advancement of the plunger is blocked by a resilient stopper.

12. A method for dispensing an intraocular lens from an injector, comprising:

arranging the intraocular lens within a receiving chamber of the injector in a folded state;

transferring the intraocular lens from the receiving chamber into a cannula by pressing on a handpiece of an axially displaceable plunger;

bringing a rotary element, mounted on a plunger rod, into engagement with a seat of a housing, including meshing an internal thread of the rotary element with an external thread of the seat; and advancing the axially displaceable plunger, while the intraocular lens is located inside the cannula, so as to dispense the intraocular lens from the cannula by alternatively further pressing on the handpiece or turning the rotary element relative to the housing such that, when the internal thread engages the external thread and a locking ring of the axially displaceable plunger abuts a wall of the rotary element, rotation of the rotary element causes axial advancement of the axially displaceable plunger.

13. An injector adapted to carry out the method according to claim 12.

* * * * *